United States Patent
Bao et al.

(10) Patent No.: US 9,970,818 B2
(45) Date of Patent: May 15, 2018

(54) SPATIALLY RESOLVED OPTICAL EMISSION SPECTROSCOPY (OES) IN PLASMA PROCESSING

(71) Applicant: TOKYO ELECTRON LIMITED, Tokyo (JP)

(72) Inventors: Junwei Bao, Los Altos, CA (US); Ching-Ling Meng, Sunnyvale, CA (US); Holger Tuitje, Fremont, CA (US); Mihail Mihaylov, San Jose, CA (US); Yan Chen, Santa Clara, CA (US); Zheng Yan, San Jose, CA (US); Haixing Zou, San Jose, CA (US); Hanyou Chu, Palo Alto, CA (US)

(73) Assignee: Tokyo Electron Limited, Tokyo (JP)

( * ) Notice: Subject to any disclaimer, the term of this patent is extended or adjusted under 35 U.S.C. 154(b) by 168 days.

(21) Appl. No.: 14/530,164

(22) Filed: Oct. 31, 2014

(65) Prior Publication Data
US 2015/0124250 A1     May 7, 2015

Related U.S. Application Data

(60) Provisional application No. 61/898,975, filed on Nov. 1, 2013.

(51) Int. Cl.
*G01J 3/30* (2006.01)
*G01J 3/443* (2006.01)
(Continued)

(52) U.S. Cl.
CPC .............. *G01J 3/443* (2013.01); *G01N 21/31* (2013.01); *G01N 21/68* (2013.01); *G01N 2201/10* (2013.01)

(58) Field of Classification Search
CPC .................................. G01J 3/443; G01N 21/68
See application file for complete search history.

(56) References Cited

U.S. PATENT DOCUMENTS 4,692,630 A * 9/1987 Gogol ................... G01N 21/62
                                                                    250/423 P
5,353,790 A * 10/1994 Jacques .............. G01N 21/4738
                                                                   250/574
(Continued)

FOREIGN PATENT DOCUMENTS

| JP | H04-303599 A | 10/1992 |
|---|---|---|
| JP | 2005-328050 A | 11/2005 |

(Continued)

OTHER PUBLICATIONS

International Patent Application No. PCT-US2014/063565, "International Search Report and Written Opinion," dated Jan. 29, 2015, International Filing Date Oct. 31, 2014.

(Continued)

*Primary Examiner* — Tri Ton
*Assistant Examiner* — Rufus Phillips
(74) *Attorney, Agent, or Firm* — Oblon, McClelland, Maier & Neustadt, L.L.P.

(57) ABSTRACT

Disclosed is a method, computer method, system, and apparatus for measuring two-dimensional distributions of optical emissions from a plasma in a semiconductor plasma processing chamber. The acquired two-dimensional distributions of plasma optical emissions can be used to infer the two-dimensional distributions of concentrations of certain chemical species of interest that are present in the plasma, and thus provide a useful tool for process development and also for new and improved processing tool development. The disclosed technique is computationally simple and inexpensive, and involves the use of an expansion of the assumed optical intensity distribution into a sum of basis functions that allow for circumferential variation of optical intensity. An example of suitable basis functions are Zernike polynomials.

19 Claims, 3 Drawing Sheets

(51) Int. Cl.
*G01N 21/31* (2006.01)
*G01N 21/68* (2006.01)

(56) References Cited

U.S. PATENT DOCUMENTS

| | | | |
|---|---|---|---|
| 5,956,138 A * | 9/1999 | Slater | G01J 3/30 356/244 |
| 6,201,628 B1 * | 3/2001 | Basiji | G01J 3/443 250/458.1 |
| 6,381,008 B1 * | 4/2002 | Branagh | G01J 3/443 356/328 |
| 6,958,484 B2 | 10/2005 | Mitrovic | |
| 7,241,397 B2 | 7/2007 | Fink et al. | |
| 7,591,923 B2 | 9/2009 | Mitrovic et al. | |
| 8,416,509 B2 * | 4/2013 | Yi | G01J 3/02 250/423 R |
| 8,513,583 B2 | 8/2013 | Corke et al. | |
| 8,553,218 B2 * | 10/2013 | Tinnemans | G01N 21/4785 356/237.5 |
| 2003/0174325 A1 | 9/2003 | Zhang | G01N 21/718 356/318 |
| 2004/0104681 A1 | 6/2004 | Mitrovic | |
| 2009/0251700 A1 * | 10/2009 | Venugopal | G01J 3/02 356/437 |
| 2013/0141720 A1 * | 6/2013 | Park | G01N 21/68 356/316 |

FOREIGN PATENT DOCUMENTS

| | | |
|---|---|---|
| JP | 2008-199014 A | 8/2008 |
| JP | 2013-021321 A | 1/2013 |
| WO | WO 2013/029957 A2 | 3/2013 |
| WO | WO 2013/095776 A1 | 6/2013 |

OTHER PUBLICATIONS

Master's Thesis of Jae-Wook Lee, presented at University of California, Berkeley, on Jul. 1, 2000.

Shannon et al., "A spatially resolved optical emission sensor for plasma etch monitoring", Appl. Phys Lett, vol. 71(11), pp. 1467-1468, 1997.

Excerpt from Gary Selwyn, "Optical Diagnostic Techniques for Plasma Processing", AVS Press, 1993. Relevant chapter 3 on optical emission spectroscopy (OES) is provided, along with title and bibliographic information pages.

Office Action dated May 23, 2017, in Korean Patent Application No. 10-2016-7014192 (with English-language translation).

Kagaku Jiten, Japan, Tokyo Kagaku Dojin, Oct. 1, 1994, 1$^{st}$ edition, p. 505.

Office Action dated Mar. 14, 2017 in corresponding JP Patent Application No. 2016-527330 (with English translation); 10 pgs.

* cited by examiner

SPATIALLY RESOLVED OPTICAL EMISSION SPECTROSCOPY (OES) IN PLASMA PROCESSING

CROSS REFERENCE TO RELATED APPLICATIONS

This application is based on and claims the benefit of and priority to co-pending U.S. Provisional Patent Application No. 61/898,975, entitled "SPATIALLY RESOLVED OPTICAL EMISSION SPECTROSCOPY (OES) IN PLASMA ETCHING" (Ref. No. TTI-242PROV), filed on Nov. 1, 2013, the entire contents of which are herein incorporated by reference.

BACKGROUND OF THE INVENTION

Field of the Invention

The present invention relates to a method, computer method, system, and apparatus for measuring concentrations of chemical species in semiconductor plasma processing using plasma optical emission spectroscopy (OES). Specifically, it relates to determining two-dimensional distributions of plasma optical emissions from which two-dimensional distributions of chemical species concentrations can be determined.

Description of Related Art

Production of semiconductor devices, displays, photovoltaics, etc., proceeds in a sequence of steps, each step having parameters optimized for maximum device yield. In plasma processing, among the controlled parameters strongly affecting yield is the chemistry of the plasma, and particularly the local chemistry of the plasma, i.e. the local concentrations of various chemical species in the plasma environment proximate the substrate being processed. Certain species, particularly transient chemical species, such as radicals have a great influence on the plasma processing outcome, and it is known that elevated local concentrations of these species can produce areas of faster processing, which may lead to nonuniformities in the processing steps and ultimately the devices being produced.

The chemistry of a plasma process is controlled in a direct or indirect manner through the control of a large number of process variables, such as one or more RF or microwave powers supplied to excite the plasma, the gas flows and kinds of gases supplied to the plasma processing chamber, the pressure in the plasma processing chamber, the type of substrate being processed, the pumping speed delivered to the plasma processing chamber, and many more. Optical emission spectroscopy (OES) has proven itself as a useful tool for process development and monitoring in plasma processing. In optical emission spectroscopy, the presence and concentrations of certain chemical species of particular interest, such as radicals, is deduced from acquired optical (i.e. light) emission spectra of the plasma, wherein the intensities of certain spectral lines and ratios thereof correlate to the concentrations of chemical species. A detailed description of the technique can be found in e.g. G. Selwyn, "Optical Diagnostic Techniques for Plasma Processing", AVS Press, 1993, and will not be repeated here, for brevity.

While the use of optical emission spectroscopy has become relatively commonplace, particularly in plasma process development, it is usually done by acquiring optical emission spectra from a single elongated volume within the plasma, inside the plasma processing chamber. The precise shape and size of this volume is determined by the optical system used to collect the optical emission from the plasma. Such collection of the optical emission signal inherently results in averaging of the plasma optical emission spectra along the length of this elongated volume, also known as a ray, and thus all the information about local variations of the plasma optical emission spectra, and thus also local variations of chemical species concentrations, are generally lost.

In development of plasma processes, and indeed even in development of new and improved plasma processing systems, it is useful to know the two-dimensional distribution of chemical species of interest above the substrate being processed, so changes in the system design and/or process parameters can be made to minimize variations of the processing outcome across the substrate, for example. A further application of the plasma optical emission spectroscopy (OES) technique is in determining the endpoint of a plasma processing step by monitoring the evolution of and abrupt change of chemical species present in the plasma that is associated with e.g. an etching step reaching a substrate layer of different chemical composition that the one that was etched during the etching process. The ability to determine the plasma processing step endpoint across the entire surface of the substrate contributes to increased device yield because of not terminating the plasma processing step prematurely.

One technique extensively used in other areas of technology, e.g. X-ray tomography, to determine a spatial distribution of a variable from known integrated measurements along multiple rays traversing the area of interest is tomographic inversion, using the Abel transform, or Radon transform. However, to be effective, this technique requires a large amount of acquired data, i.e. a large number of rays, which is impractical in a semiconductor processing tool that has limited optical access to the plasma through one or a small number of windows or optical ports built into the plasma processing chamber wall. Tomographic techniques are generally also very computationally intensive. It has also been found that local variations of chemical species concentrations are of a generally smooth nature, without any abrupt gradients in both the radial, and even more so in the circumferential (i.e. azimuthal) direction. Thus, it would be advantageous to have a simple, fast, and relatively low cost plasma optical emission spectroscopy (OES) technique and system that is capable of acquiring the two-dimensional distributions of plasma optical emission spectra without the overhead involved in tomographic approaches to OES measurements.

Most notably, while the variations in the circumferential direction may be small, they are not nonexistent, as some prior techniques presume, and the ideal technique and system would still have to be able to reliably capture these variations.

SUMMARY OF THE INVENTION

An aspect of the invention includes a method for determining a spatial distribution of plasma optical emission, comprising: igniting a plasma in a plasma processing chamber, the plasma processing chamber having a plasma optical emission measurement system, the plasma optical emission measurement system having a controller for controlling the plasma optical emission measurement system; using the plasma optical emission measurement system, measuring N plasma optical emission spectra integrated along N non-coincident rays across the plasma processing chamber, where N>1, each measured optical emission spectrum comprising M wavelengths, where M≥1; selecting, using the controller, an optical intensity distribution function $I(r, \theta)$ comprising a sum of N basis functions $F_p(r, \theta)$ $$I(r, \theta) = \sum_{p=1}^{N} a_p F_p(r, \theta)$$

wherein at least one of the N basis functions $F_p(r, \theta)$ varies with both radial location r and circumferential location $\theta$ inside the plasma processing chamber, and wherein each of the N basis functions $F_p(r, \theta)$ is associated with a fitting parameter $\alpha_p$; and determining, using the controller, a spatial distribution of plasma optical emission for each of the M wavelengths by fitting the N fitting parameters $\alpha_p$ of the selected optical intensity distribution function $I(r, \theta)$, to fit the selected optical intensity distribution function $I(r, \theta)$ to the N measured plasma optical emission spectra. In an embodiment, the N basis functions $F_p(r, \theta)$ may be Zernike polynomials $Z_p(r, \theta)$, or more specifically the N lowest order Zernike polynomials $Z_p(r, \theta)$.

Another aspect of the invention includes a plasma optical emission measurement system that comprises: N separate optical systems for each of N rays across the plasma processing chamber, each optical system collecting plasma optical emission spectra through at least one optical window disposed at a wall of the plasma processing chamber, and each optical system being coupled to a multi-channel spectrometer for measuring the plasma optical emission spectra.

An alternative embodiment includes a plasma optical emission measurement system that comprises: an optical system for collecting plasma optical emission spectra through an optical window disposed at a wall of the plasma processing chamber, the optical system comprising: a scanning mirror configured to scan a plurality of non-coincident rays across the plasma processing chamber; and a spectrometer coupled to the optical system for measuring the plasma optical emission spectra.

Yet another embodiment of the invention includes a telecenter coupler for collecting an optical signal from the plasma and directing the optical signal to an end of an optical fiber for transmitting the optical signal to the multi-channel spectrometer, the telecenter coupler including: at least one collection lens; at least one coupling lens; and an optional aperture.

BRIEF DESCRIPTION OF THE DRAWINGS

A more complete appreciation of the invention and many of the attendant advantages thereof will become readily apparent with reference to the following detailed description, particularly when considered in conjunction with the accompanying drawings, in which.

DETAILED DESCRIPTION OF EXEMPLARY EMBODIMENTS

In the following description, in order to facilitate a thorough understanding of the invention and for purposes of explanation and not limitation, specific details are set forth, such as particular geometries of a plasma optical emission spectroscopy (OES) system, and descriptions of various components and processes. However, it should be understood that the invention may be practiced in other embodiments that depart from these specific details.

In the description to follow, the term substrate, which represents the workpiece being processed, may be used interchangeably with terms such as semiconductor wafer, LCD panel, light-emitting diode (LED), photovoltaic (PV) device panel, etc., the processing of all of which falls within the scope of the claimed invention.

Reference throughout this specification to "one embodiment" or "an embodiment" means that a particular feature, structure, material, or characteristic described in connection with the embodiment is included in at least one embodiment of the invention, but do not denote that they are present in every embodiment. Thus, the appearances of the phrases "in one embodiment" or "in an embodiment" in various places throughout this specification are not necessarily referring to the same embodiment of the invention. Furthermore, the particular features, structures, materials, or characteristics may be combined in any suitable manner in one or more embodiments.

Various operations will be described as multiple discrete operations in turn, in a manner that is most helpful in understanding the invention. However, the order of description should not be construed as to imply that these operations are necessarily order dependent. In particular, these operations need not be performed in the order of presentation. Operations described may be performed in a different order than the described embodiment. Various additional operations may be performed and/or described operations may be omitted in additional embodiments.

Figure 1:
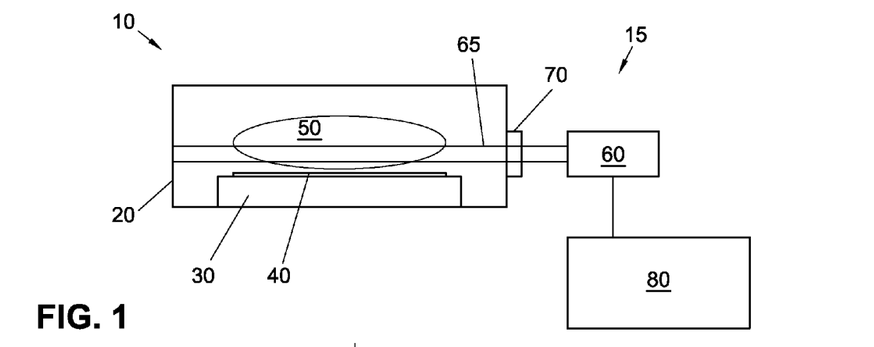
FIG. 1 is a side view schematic of a plasma processing system equipped with an OES measurement system in accordance with an embodiment of the invention.

FIG. 1 shows an embodiment of a plasma processing system 10 equipped with a plasma optical emission spectroscopy (OES) system 15. Plasma processing system 10 comprises plasma processing chamber 20, inside which a substrate holder 30 is disposed, such as an electrostatic chuck, for receiving a substrate 40 to be processed. RF and/or microwave power is supplied to the plasma processing chamber 20 (not shown) to ignite and sustain a plasma 50 proximate the substrate 40, wherein the energetic chemical species from the plasma 50 are used to perform a plasma processing step on substrate 40. Processing gases are flown into the plasma processing chamber 20 (not shown) and a pumping system is provided (not shown) to maintain a vacuum in the plasma processing chamber 20, at a desired process pressure. Examples of plasma processing steps include plasma etching, plasma-enhanced chemical vapor deposition (PECVD), plasma-enhanced atomic layer deposition (PEALD), etc. The system and method described herein are applicable to any kind of plasma processing.

The plasma optical emission spectroscopy (OES) system 15 is used to acquire plasma optical emission spectra via at least one optical detector 60, which communicates the acquired plasma optical emission spectra to and is controlled by controller 80. Controller 80 may be a general purpose computer, and may be located proximate to plasma processing system 10, or may be located remotely, and connected via an intranet or internet connection to optical detector 60.

Optical detector 60 has optics configured in such a way that it collects plasma optical emissions from an elongated, generally pencil-shaped volume of space 65 within the plasma 50. Optical access to the plasma processing chamber is provided by optical window 70. Optical window 70 can comprise a material such as glass, quartz, fused silica, or sapphire, depending on the application and how aggressive the chemistry of the plasma 50 is. The volume 65, hereinafter referred to as a "ray" 65, defines the portion of space from which the plasma optical emission spectra are collected, and the collected spectra represent an integral of contributions to the collected plasma optical emission spectrum from all points located along and within the ray 65. It should be noted that depending on the geometry and configuration of optical detector 60, the contributions of each point within the ray 65 will not be equal, but are weighted and governed by the optical efficiency (to be discussed in more detail later). In a typical configuration, the ray 65 is oriented substantially parallel with the surface of substrate 40 and is maintained at a small distance from the surface of substrate 40, so as to reduce optical interference from the substrate surface, yet is kept close enough to the substrate 40 to sample the plasma chemistry proximate the substrate surface.

Controller 80, as mentioned before, is used to control the plasma optical emission spectroscopy (OES) system 15, and to also compute the (1) plasma optical intensity distribution as a function of spatial location and wavelength, and to compute (2) the spatial distribution of chemical species of interest from the computed plasma optical intensity distribution. This information can then be used for process development, plasma processing tool development, in-situ plasma process monitoring, plasma process fault detection, plasma process endpoint detection, etc.

Figures 2, 3:
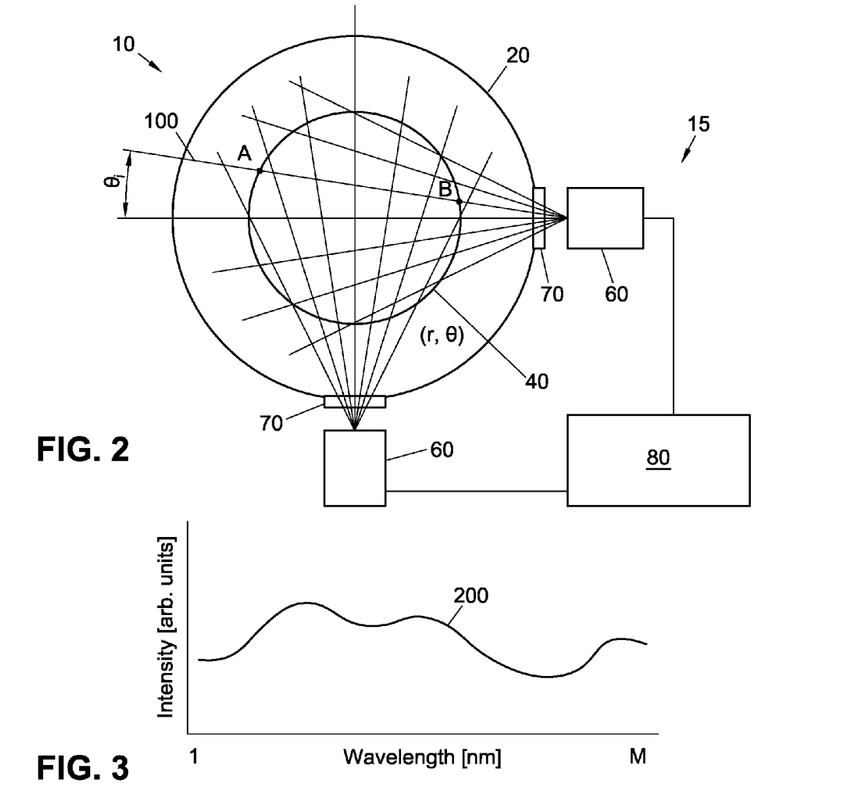
FIG. 2 is a top view schematic of a plasma processing system equipped with an OES measurement system in accordance with an embodiment of the invention.
FIG. 3 is an exemplary plasma optical emission spectrum acquired using the OES measurement system in accordance with an embodiment of the invention.

FIG. 1 shows one ray 65 traversing the plasma 50 located within the plasma processing chamber 20, proximate substrate 40 being processed. In an embodiment of the invention, multiple rays 100 can be used to sample the plasma optical emission spectra, as shown in FIG. 2, which shows the top schematic view of the plasma processing system 10 of e.g. FIG. 1. In the exemplary embodiment of FIG. 2, two optical detectors 60 are used to collect plasma optical emission spectra, each from 7 rays 100. The rays 100 need to be non-coincident such that the largest amount of spatial information is acquired from the plasma 50 above substrate 40. The number of rays 100 per optical detector 60 can vary from 2 to 9, and higher. Also, in another embodiment, where optical access is provided to plasma processing chamber 20 by only a single optical window 70, a single optical detector 60 can be used with its associated fan of rays 100. Alternatively, a third or more optical detectors, each with an associated ray fan, may be used. The angle of each ray 100 is defined with respect to the centerline of its optical detector 60, as $\theta_i$. Every point within the plasma processing chamber can be defined by its polar coordinates, i.e. $(r, \theta)$, as shown in FIG. 2.

As will be described in greater detail later, depending on the configuration of optical detector 60, all plasma optical emission spectra from the associated fan of rays 100 can be collected simultaneously. This is suitable for embodiments of optical detector 60 with multiple optical systems and channels, allowing simultaneous collection from all rays 100. Alternatively, the plasma optical emission spectra can be acquired sequentially along rays 100 associated with an optical detector 60. The latter is suitable in scanning embodiments, where plasma optical emission spectra are collected as the ray 100 is scanned from one angle $\theta_i$ to another. Understandably, this scanning and acquisition needs to occur fast enough such that rapid changes in the plasma chemistry can be detected across the entire substrate.

FIG. 3 shows an example plasma optical emission spectrum acquired from one ray 100, at angle $\theta_i$, using one optical detector 60. In the spectrum, intensities of M wavelengths are collected, typically ranging from about 200 nm to about 800 nm. CCDs of typical spectrometers employed for optical emission spectroscopy have 4096 pixels spanning the wavelength range, but the number of pixels can vary as low as 256 and as high as 65536, depending on the application and required resolution of the collected spectra.

Plasma optical emission spectra collected by optical detectors 60 from their associated fans of rays 100 are communicated to controller 80, which is used to further process the communicated data to compute the spatial distribution of plasma optical emission, and from there the spatial distribution of chemical species concentrations. An aspect of the present invention is an algorithm for fast calculation of the spatial distribution of plasma optical emissions for each wavelength, which allows in-situ monitoring of plasma processes, for endpoint detection, fault detection, etc.

Figure 4:
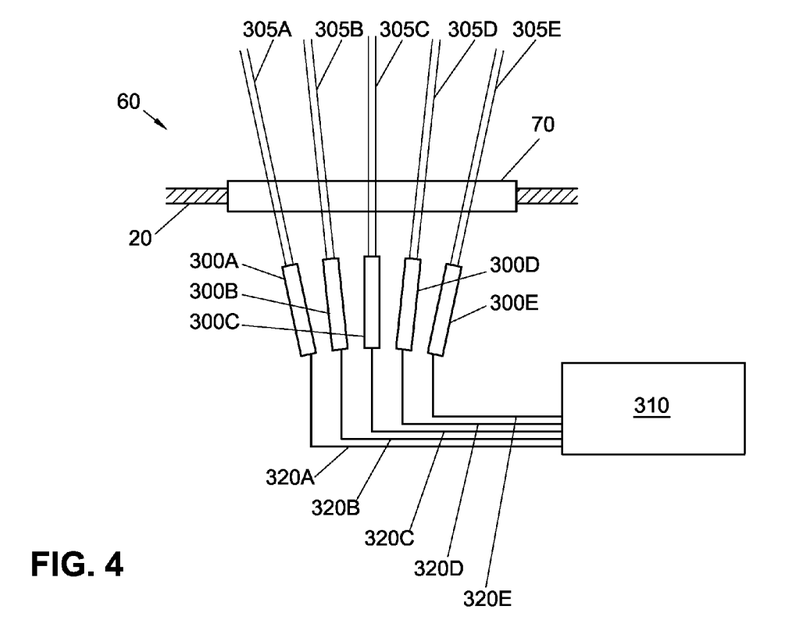
FIG. 4 is a schematic of an optical system for use in the OES measurement system, in accordance with an embodiment of the invention.

FIG. 4 shows an embodiment of optical detector 60 wherein a single multi-channel spectrometer 310 is used to collect plasma optical emission spectra from rays 305A-E simultaneously. The exemplary embodiment shown here has 5 rays 305A-E, for clarity, but the number can vary from 2 to 9, and even higher than 9. The optical detector 60 comprises optical systems 300A-E for each ray 305A-E, all located proximate optical window 70 mounted on the wall of plasma processing chamber 20. Rays 305A-E are arranged in a diverging manner, so as to cover the relevant portion of substrate 40 (not shown). Collected plasma optical emission spectra are fed into the multi-channel spectrometer 310 from optical systems 300A-E, via respective optical fibers 320A-E. Optical systems 300A-E will be described in greater detail later. The embodiment of FIG. 4 is suitable for fast diagnostics, because of its ability to collect plasma optical emission spectra simultaneously.

Figure 5:
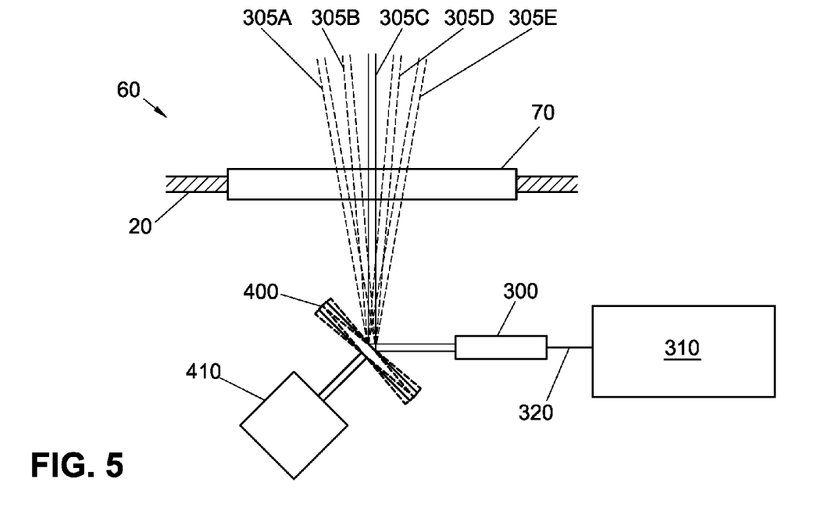
FIG. 5 is a schematic of an optical system for use in the OES measurement system, in accordance with another embodiment of the invention.

FIG. 5 shows an alternative embodiment in which a single channel spectrometer 310 is used, and rays 305A-E are formed by a scanning mirror 400 which is controllably scanned to sweep out rays 305A-E while plasma optical emission spectra are acquired by the spectrometer 310 via a single optical system 300, which will be described in greater detail later. This embodiment is suitable for sequential collection of plasma optical emission spectra, and therefore is more suited for diagnostics of slower-evolving plasma processes. The scanning mirror 400 can be mounted and actuated by a galvanometer stage 410. Alternatively, the scanning mirror 400 may be mounted on and scanned by a stepper motor 410. The number of rays 305A-E here is shown as 5, but in practice it is determined by the settings in the controller software for controlling the galvanometer stage or stepper motor 410.

To ensure that a precise volume of space is sampled, the optical systems 300A-E of FIG. 4 and optical system 300 of FIG. 5 need to be configured such that rays 305A-E are collimated, with as small a divergence angle as can feasibly be achieved for a given target cost of the optical system.

Figure 6:
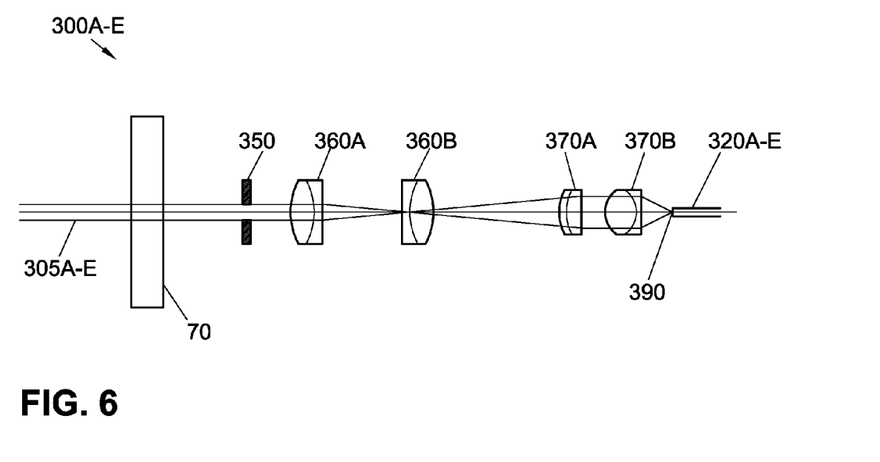
FIG. 6 is an expanded schematic view of an embodiment of an optical system in accordance with an embodiment of the invention.

An exemplary embodiment of optical systems 300A-E and 300 is shown in FIG. 6. The optical system 300A-E, also known as a telecenter coupler, has the task of collecting plasma optical emission spectra from a volume of space within the plasma 50 defined by rays 305A-E, and directing the collected plasma optical emission spectra to the end 390 of an optical fiber 320A-E, or 320, so it can be transmitted to the spectrometers 310 of embodiments of FIG. 4 or 5. The diameter of the rays 305A-E is defined by an optional aperture 350, formed in a plate. In an alternative embodiment, other optical components, such as lenses can be used to define the diameter of the rays 305A-E. An example ray diameter is 4.5 mm but it can vary from about 1 mm to 20 mm, depending on the application. The collected rays 305A-E are passed through a combination of collection lenses 360A and 360B which in combination with the optional aperture define the rays 305A-E. The numerical aperture of the collection system and rays 305A-E is generally very low, for example, approximately 0.005, and the resultant rays 305A-E are essentially collimated, with minimal divergence angle. On the other end of optical system 300A-E or 300 is another pair of lenses, i.e. coupling lenses 370A and 370B, which serve to focus the collected optical emission spectra onto the end 390 of the optical fiber 320A-E, or 320. All lenses used in the system are preferably achromatic, or even apochromatic for more demanding applications, which ensures that the focal length of each lens does not vary with wavelength, such that the optical system 300A-E, or 300, operates satisfactorily over a large range of wavelengths, typically from 200 nm to 800 nm, but in some cases going as low as 150 nm. For better performance in the UV part of the spectrum, i.e. 350 nm and less, UV-grade materials are to be used for all optical components.

For every optical hardware configuration, it is important to know the optical efficiency w which is a weighting factor that applies to all points within rays 305A-E from which plasma optical emission spectra are acquired. The optical efficiency w can be determined by simulation, using optical design software, or by experiment using calibrated light sources and moving them across and along rays 305A-E to determine the efficiency of coupling of light from a given location within a ray 305A-E to the optical fiber end 390. The optical efficiencies w will be used in the algorithm for determining the spatial distribution of plasma optical emissions.

As mentioned before, the task of the plasma optical emission spectroscopy (OES) system 15 is the determination of the two-dimensional intensity distribution of the plasma optical emission, for each of M measured wavelengths λ.

For each ray 100 of FIG. 2, the ray being denoted mathematically by an index i, the collected optical detector output $D_i$ can be defined as $$D_i = \int_{l_{AB}} I(r, \theta) w(r, \theta) dl$$

where $I(r, \theta)$ is the plasma optical emission intensity at a location $(r, \theta)$ within and along the ray 100, and $w(r, \theta)$ is the optical efficiency for collection of light from location $(r, \theta)$ by optical detector i. The resultant optical detector output $D_i$ represents an integral of the product of these quantities along a straight path from point A to point B on the circumference of the substrate (see FIG. 2), the contributions from plasma outside the circumference of substrate 40 being neglected in this model (this is a valid assumption because the plasma density and thus plasma light emission is generally low in these areas).

In a plasma optical emission spectroscopy (OES) system 15 with N optical detectors and rays, or alternatively N scanned positions of rays 100, there are N collected intensities for each of M measured wavelengths λ. Therefore, to reconstruct a spatial distribution of plasma optical emission at one wavelength λ, a functional form with N parameters has to be assumed. Given the restricted number N of parameters, a judicious choice of basis functions for the distribution of plasma optical emission needs to be made. The selected basis functions need to vary both with radial coordinate r, and also the circumferential coordinate θ for them to be able to reproduce satisfactorily the circumferential variations of plasma emission across the substrate 40.

One class of basis functions particularly well suited to this task are Zernike polynomials $Z_p(r, \theta)$. Zernike polynomials are defined as a product of a term dependent on radial coordinate r and a term dependent on the circumferential coordinate θ, i.e.

$$Z_p(r, \theta) = R(r) G(\theta)$$

Table 1 lists the first 18 order Zernike polynomials, herein denoted using commonly used mathematical notation $Z_n^m$.

TABLE 1

The first 18 order Zernike polynomials $Z_n^m$.

| Order | n | m | $R(r)G(\theta)$ |
|---|---|---|---|
| 0 | 0 | 0 | 1 |
| 1 | 1 | 1 | $2r \cos \theta$ |
| 2 | 1 | -1 | $2r \sin \theta$ |
| 3 | 2 | 2 | $\sqrt{6} r^2 \cos 2\theta$ |
| 4 | 2 | 0 | $\sqrt{3}(2r^2 - 1)$ |
| 5 | 2 | -2 | $\sqrt{6} r^2 \sin 2\theta$ |
| 6 | 3 | 3 | $\sqrt{8} r^3 \cos 3\theta$ |
| 7 | 3 | 1 | $\sqrt{8}(3r^3 - 2r)\cos \theta$ |
| 8 | 3 | -1 | $\sqrt{8}(3r^3 - 2r)\sin \theta$ |
| 9 | 3 | -3 | $\sqrt{8} r^3 \sin 3\theta$ |
| 10 | 4 | 4 | $\sqrt{10} r^4 \cos 4\theta$ |
| 11 | 4 | 2 | $\sqrt{10}(4r^3 - 3r^2)\cos 2\theta$ |
| 12 | 4 | 0 | $\sqrt{5}(6r^4 - 6r^2 + 1)$ |
| 13 | 4 | -2 | $\sqrt{10}(4r^3 - 3r^2)\sin 2\theta$ |
| 14 | 4 | -4 | $\sqrt{10} r^4 \sin 4\theta$ |
| 15 | 5 | 5 | $\sqrt{12} r^5 \sin 5\theta$ |
| 16 | 5 | 3 | $\sqrt{12}(5r^5 - 4r^3)\cos 3\theta$ |
| 17 | 5 | 1 | $\sqrt{12}(10r^5 - 12r^3 + 3r)\cos \theta$ |

In general, other basis functions can be chosen in this application, as long as they are orthogonal and as long as their derivatives are continuous over the unit circle, just as is the case with Zernike polynomials. However, Zernike polynomials are preferred in this application because of their property that a relatively small number of terms can be used to describe quite complex variations of a function in polar coordinates, both radial and circumferential.

Substituting Zernike polynomials $Z_p(r, \theta)$ into the collected detector output results in $$D_i = \int_A^B w(r, \theta) \sum_{p=1}^N a_p Z_p(r, \theta) dl = \int_A^B w(r, \theta) \sum_{p=1}^N a_p R_p(r) G(\theta) dl$$

where $a_p$ are fitting parameters associated with every basis function, i.e. Zernike polynomial order.

Now that the collected detector output $D_i$ is defined in terms of the selected basis functions, fitting parameters, and optical efficiency, the problem of determining the fitting parameters $a_p$ of $D_i$ is reduced to minimizing the following, i.e. solving the least squares problem $$\min\left\{\sum_{i=1}^{N}(D_i - D_i^{measured})^2\right\}$$

or $$\min\left\{\sum_{i=1}^{N}\left(\int_{A}^{B} w(r,\theta)\sum_{p=1}^{N} a_p R_p(r)G(\theta)dl - D_i^{measured}\right)^2\right\}$$

where $D_i^{measured}$ represent the measured plasma optical spectra intensities at ray i. This minimization algorithm needs to be repeated for each of M measured wavelengths $\lambda$. Many methods are known in the art for solving this least squares problem. Because the dimension of the least squares problem is relatively small it can be efficiently solved for all wavelengths, for each instant in time that plasma optical emission spectra are measured; and furthermore such calculations can be repeated in rapid succession enabling the determination of rapidly evolving two-dimensional distributions of plasma optical emissions for large numbers M of wavelengths. From these one can then determine the time-evolving two-dimensional distributions of chemical species concentrations across the substrate 40, which can be used for endpoint detection, fault detection, process development, processing tool development, etc.

Figure 7:
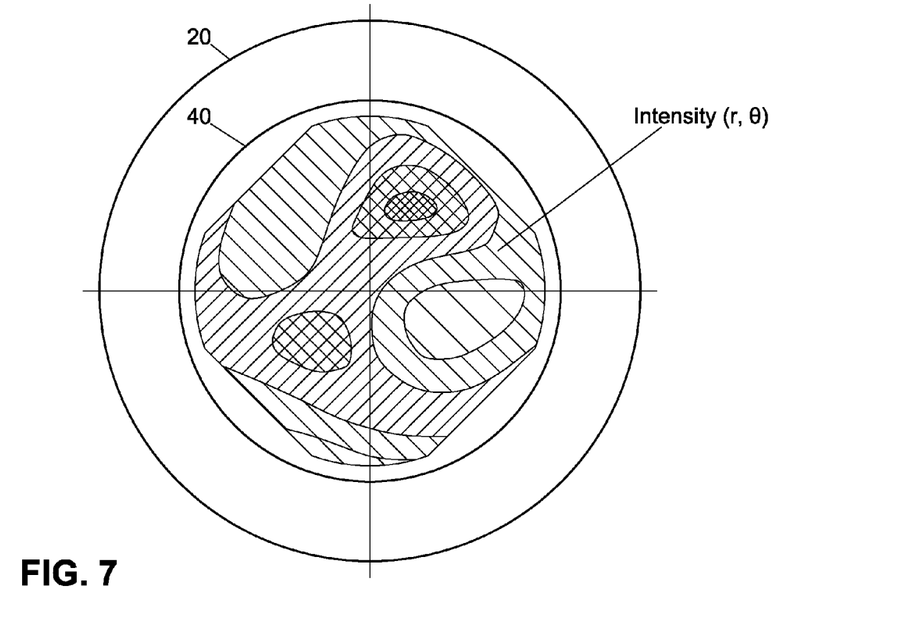
FIG. 7 is an exemplary two-dimensional distribution of plasma optical emission measured using the OES measurement system and associated method in accordance with an embodiment of the invention.

FIG. 7 shows an example of one such plasma optical emission intensity distribution determined with the method in accordance with an embodiment of the invention. The depicted distribution clearly shows good capture of both radial and circumferential variations in the plasma optical emission intensity, despite a relatively low number of terms, i.e. N=18.

Persons skilled in the relevant art can appreciate that many modifications and variations are possible in light of the above teaching. Persons skilled in the art will recognize various equivalent combinations and substitutions for various components shown in the figures. It is therefore intended that the scope of the invention be limited not by this detailed description, but rather by the claims appended hereto.

What is claimed is:

1. A method for determining a spatial distribution of plasma optical emission, comprising:
   igniting a plasma in a plasma processing chamber, the plasma processing chamber having a plasma optical emission measurement system, the plasma optical emission measurement system having a controller for controlling the plasma optical emission measurement system;
   using the plasma optical emission measurement system, measuring N plasma optical emission spectra integrated along each of N respective non-coincident rays across the plasma processing chamber, where N>1, each measured optical emission spectrum comprising M wavelengths, where M≥1
   selecting, using the controller, an optical intensity distribution function $I(r, \theta)$ comprising a sum of N basis functions $F_p(r, \theta)$ $$I(r,\theta) = \sum_{p=1}^{N} a_p F_p(r,\theta)$$

wherein at least one of the N basis functions $F_p(r, \theta)$ varies with both radial location r and circumferential location $\theta$ inside the plasma processing chamber, and wherein each of the N basis functions $F_p(r, \theta)$ is associated with a fitting parameter $\alpha_p$; and
   determining, using the controller, a spatial distribution of plasma optical emission for each of the M wavelengths by fitting the N fitting parameters $\alpha_p$ of the selected optical intensity distribution function $I(r, \theta)$, to fit the selected optical intensity distribution function $I(r, \theta)$ to the N measured plasma optical emission spectra, wherein the step of fitting N fitting parameters $\alpha_p$ comprises utilizing an optical collection efficiency w for each one of the N non-coincident rays, each optical collection efficienc being adapted to each ray by performing a simulation or an experiment which determines the efficiency of coupling of light from a given location within each one of the N non-coincident rays to a respective optical fiber connected to a spectrometer.

2. The method of claim 1, wherein the N basis functions $F_p(r, \theta)$ are Zernike polynomials $Z_p(r, \theta)$.

3. The method of claim 1, wherein the N basis functions $F_p(r, \theta)$ are the N lowest order Zernike polynomials $Z_p(r, \theta)$.

4. The method of claim 1, wherein the step of fitting N fitting parameters $\alpha_p$ comprises least squares fitting.

5. The method of claim 1, wherein optical collection efficiency was determined by simulation.

6. The method of claim 1, wherein optical collection efficiency was determined experimentally.

7. The method of claim 1, wherein the plasma optical emission measurement system comprises:
   N separate optical systems for each of N rays across the plasma processing chamber, each optical system collecting plasma optical emission spectra through at least one optical window disposed at a wall of the plasma processing chamber, and each optical system being coupled to a multi-channel spectro er for measuring the plasma optical emission spectra.

8. The method of claim 7, wherein each optical system comprises:
   a telecenter coupler for collecting an optical signal from the plasma and directing the optical signal to an end of an optical fiber for transmitting the optical signal to the multi-channel spectrometer.

9. The method of claim 8, wherein each telecenter coupler comprises:
   at least one collection lens;
   at least one coupling lens; and
   an optical aperture.

10. The method of claim 9, wherein the at least one collection lens or the at least one coupling lens are achromatic lenses.

11. The method of claim 1, wherein the plasma optical emission measurement system comprises:
   an optical system for collecting plasma optical emission spectra through an optical window disposed at a wall of the plasma processing chamber, the optical system comprising:

a scanning mirror configured to scan a plurality of non-coincident rays from within the processing chamber, across the plasma processing chamber; and a spectrometer coupled to the optical system for measuring the plasma optical emission spectra.

12. The method of claim 11, wherein the scanning mirror is mounted on and scanned by a galvanometer scanning stage.

13. The method of claim 11, wherein the scanning mirror is mounted on and scanned by a stepper motor.

14. The method of claim 11, wherein the optical system comprises:

a telecenter coupler for collecting an optical signal from the plasma and directing the optical signal to an end of an optical fiber for transmitting the optical signal to the spectrometer.

15. The method of claim 11, wherein the telecenter coupler comprises:

at least one collection lens;
at least one coupling lens; and
an optional aperture.

16. The method of claim 15, wherein the at least one collection lens or the at least one coupling lens are achromatic lenses.

17. The method of claim 1, wherein each optical collection efficiency w is adapted to each ray by performing a calibration, wherein light sources are moved along each ray to separately determine the efficiency for each ray of coupling light to an optical fiber connected to a spectrometer.

18. A non-transitory machine-accessible storage medium having instructions stored thereon which cause a controller to perform a method for determining a spatial distribution of plasma optical emission, the method comprising:

igniting a plasma in a plasma processing chamber, the plasma processing chamber having a plasma optical emission measurement system, the plasma optical emission measurement system having a controller for controlling the plasma optical emission measurement system;

using the plasma optical emission measurement system, measuring N plasma optical emission spectra integrated along each of N respective non-coincident rays across the plasma processing chamber, where N>1, each measured optical emission spectrum comprising M wavelengths, where M≥1;

selecting, using the controller, an optical intensity distribution function $I(r, \theta)$ comprising a sum of N basis functions $F_p(r, \theta)$ $$I(r, \theta) = \sum_{p=1}^{N} a_p F_p(r, \theta)$$

wherein at least one of the N basis functions $F_p(r, \theta)$ varies with both radial location r and circumferential location $\theta$ inside the plasma processing chamber, and wherein each of the N basis functions $F_p(r, \theta)$ is associated with a fitting parameter $\alpha_p$; and determining, using the controller, a spatial distribution of plasma optical emission for each of the M wavelengths by fitting the N fitting parameters $\alpha_p$ of the selected optical intensity distribution function $I(r,\theta)$, to fit the selected optical intensity distribution function $I(r, \theta)$ to the N measured plasma optical emission spectra, wherein the fitting N fitting parameters $\alpha_p$ comprises utilizing optical collection efficiency w for each one of the N non-coincident rays, each optical collection efficiency w being adapted to each ra by performing simulation or an experiment which determines the efficiency of coupling of light from a given location within each one of the N non-coincident rays to a respective optical fiber connected to a spectrometer.

19. The storage medium of claim 18, wherein the N basis functions $F_p(r, \theta)$ are Zernike polynomials $Z_p(r, \theta)$.

* * * * *

UNITED STATES PATENT AND TRADEMARK OFFICE
CERTIFICATE OF CORRECTION

PATENT NO. : 9,970,818 B2
APPLICATION NO. : 14/530164
DATED : May 15, 2018
INVENTOR(S) : Junwei Bao et al.

Page 1 of 1

It is certified that error appears in the above-identified patent and that said Letters Patent is hereby corrected as shown below:

In the Claims

Column 9, Line 64, Claim 1, "M≥1" should read --M≥1;--;

Column 10, Line 21, Claim 1, "efficienc" should read --efficiency $w$--;

Column 10, Line 45, Claim 7, "spectro er" should read --spectrometer--;

Column 12, Line 6, Claim 18, "M≥1 ;" should read --M≥1;--; and

Column 12, Line 31, Claim 18, "ra" should read --ray--.

Signed and Sealed this
Sixteenth Day of July, 2019

Andrei Iancu
*Director of the United States Patent and Trademark Office*